United States Patent [19]
Scanlon

[11] Patent Number: 5,566,822
[45] Date of Patent: Oct. 22, 1996

[54] SUTURE RETAINER

[75] Inventor: Christopher Scanlon, Milford, Conn.

[73] Assignee: United States Surgical Corporation, Norwalk, Conn.

[21] Appl. No.: 437,246

[22] Filed: May 8, 1995

Related U.S. Application Data

[63] Continuation of Ser. No. 164,522, Dec. 9, 1993, abandoned.

[51] Int. Cl.⁶ ..................................................... A61B 17/06
[52] U.S. Cl. .......................................... 206/63.3; 206/383
[58] Field of Search ................................... 206/63.3, 380, 206/382, 383, 443

[56] References Cited

U.S. PATENT DOCUMENTS

| | | |
|---|---|---|
| 2,583,043 | 1/1952 | Dean . |
| 2,692,676 | 10/1954 | Grover . |
| 3,338,401 | 8/1967 | Regan, Jr. . |
| 3,647,057 | 3/1972 | Ashmead et al. . |
| 3,972,418 | 8/1976 | Schuler et al. . |
| 3,985,227 | 10/1976 | Thyen et al. . |
| 4,034,850 | 7/1977 | Mandel et al. . |
| 4,120,395 | 10/1978 | Mandel et al. . |
| 4,135,623 | 1/1979 | Thyen . |
| 4,183,431 | 1/1980 | Schmidt et al. . |
| 4,326,630 | 4/1982 | Bacino et al. ................... 206/63.3 X |
| 4,391,365 | 7/1983 | Batchelor . |
| 4,572,363 | 2/1986 | Alpern . |
| 4,615,435 | 10/1986 | Alpern et al. . |
| 4,884,681 | 12/1989 | Roshdy et al. . |
| 4,887,710 | 12/1989 | Roshdy et al. . |
| 4,896,767 | 1/1990 | Pinheiro . |
| 4,946,043 | 8/1990 | Roshdy et al. . |
| 4,961,498 | 10/1990 | Kalinski et al. . |
| 4,967,902 | 11/1990 | Sobel et al. . |
| 5,024,322 | 6/1991 | Holzwarth . |
| 5,052,551 | 10/1991 | Cerwin et al. . |
| 5,056,658 | 10/1991 | Sobel et al. . |
| 5,099,994 | 3/1992 | Kalinski et al. . |
| 5,101,968 | 4/1992 | Henderson et al. . |
| 5,123,528 | 6/1992 | Brown et al. . |
| 5,127,518 | 7/1992 | Holzwarth et al. . |
| 5,129,511 | 7/1992 | Brown et al. . |
| 5,154,283 | 10/1992 | Brown . |
| 5,279,411 | 1/1994 | Brunken ................................. 206/63.3 |
| 5,307,924 | 5/1994 | Manosalva et al. ..................... 206/63.3 |

FOREIGN PATENT DOCUMENTS

| | | |
|---|---|---|
| 2455880 | 12/1980 | France . |
| 2148232 | 5/1985 | United Kingdom . |

Primary Examiner—Jacob K. Ackun

[57] ABSTRACT

A suture retainer includes a base member defining a plurality of adjacent elongated enclosed suture compartments for storing sutures, a needle retaining panel connected to the base member and having a needle park for securing needles attached to the sutures and a cover panel adapted to fold onto the secured needles to enclose the needles. The suture compartments are open at a first end portion thereof to facilitate insertion of suture portion therein.

18 Claims, 5 Drawing Sheets

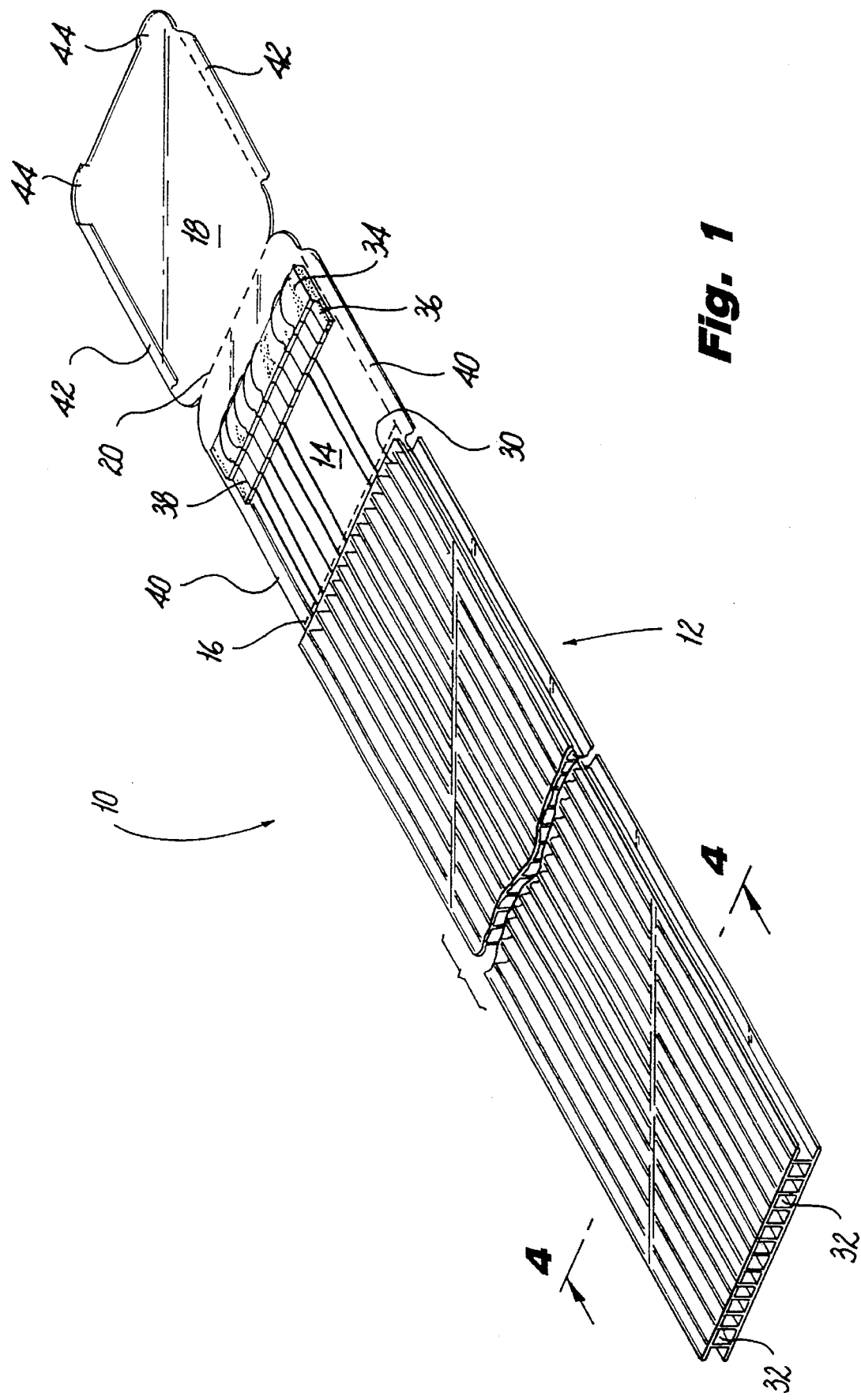

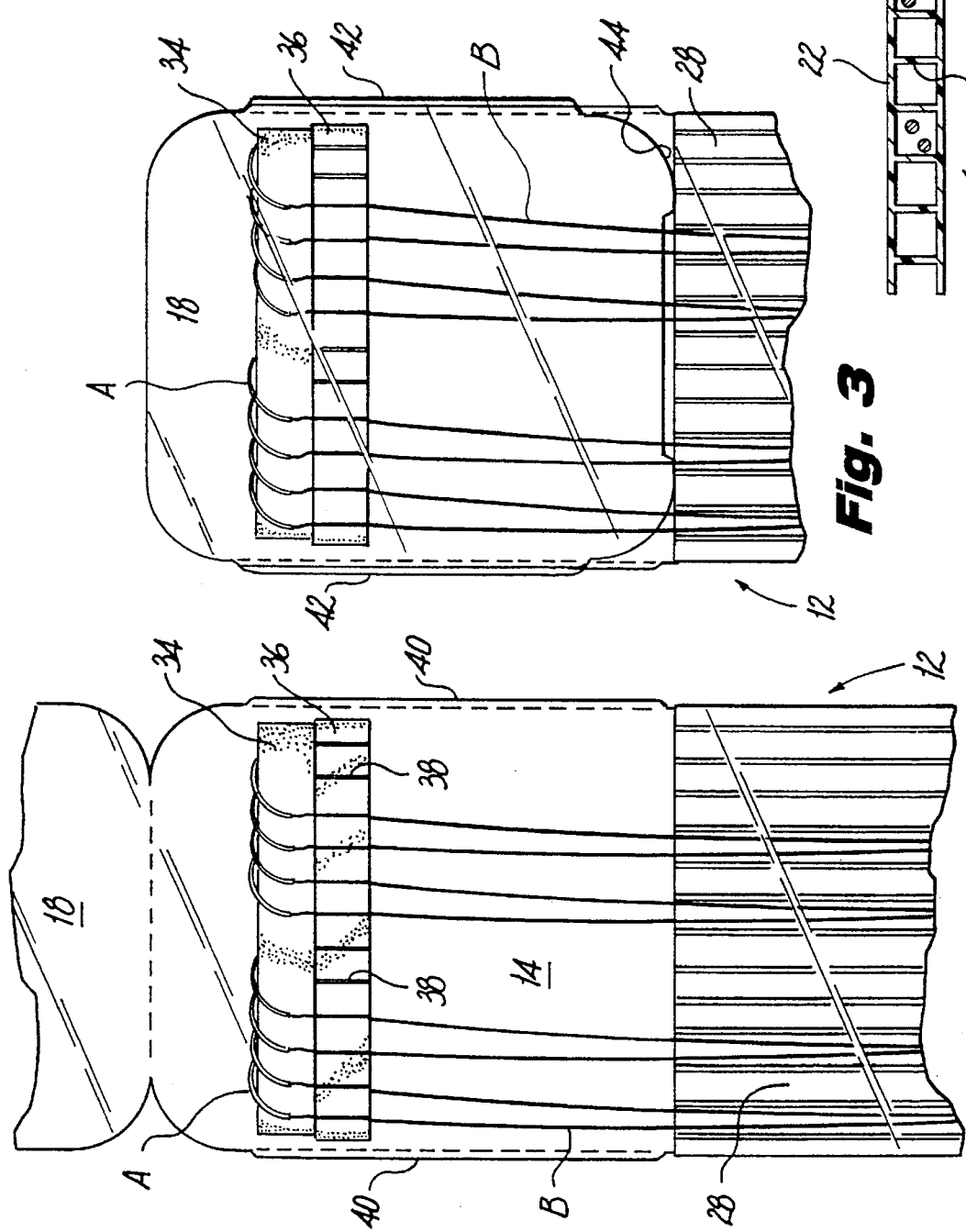

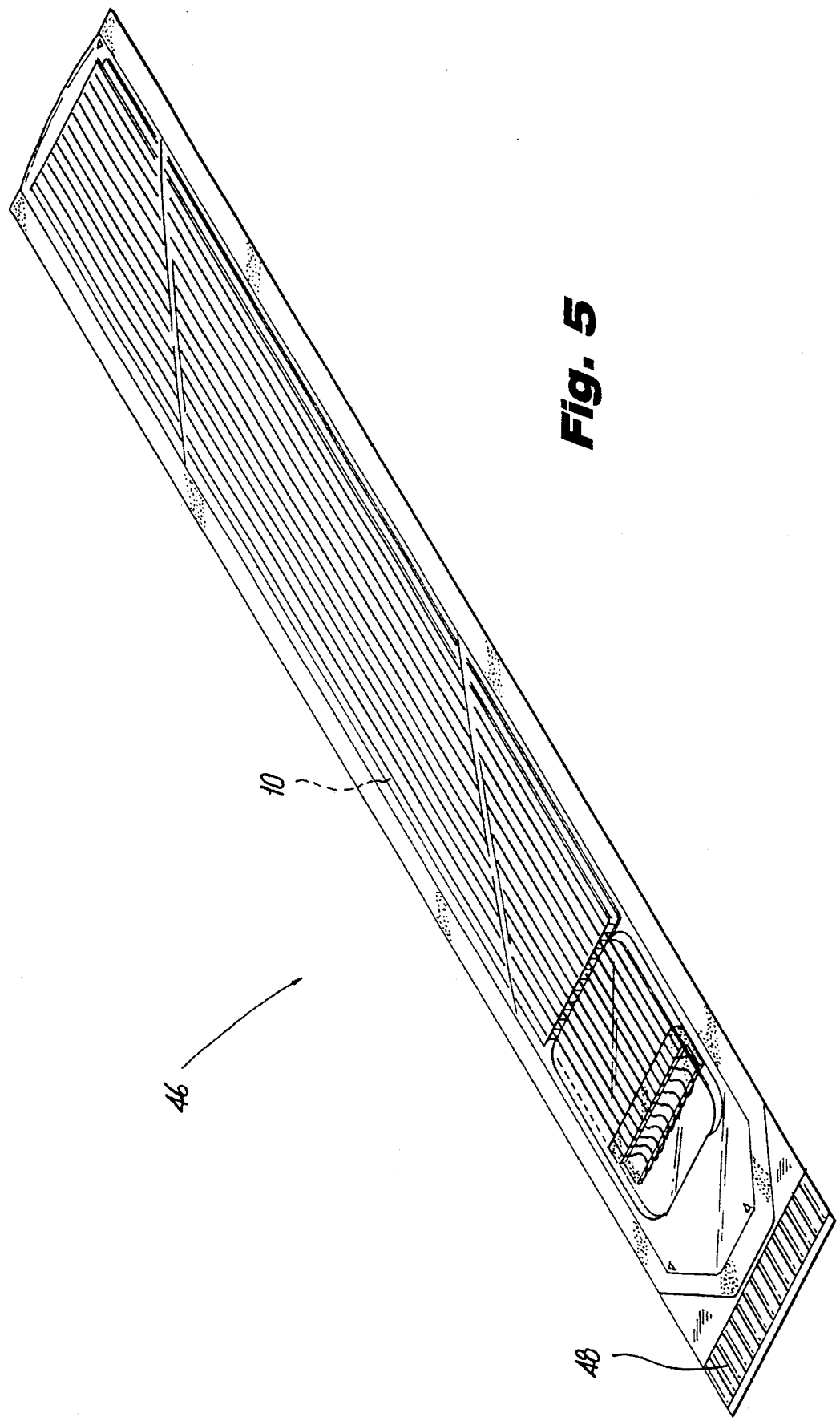

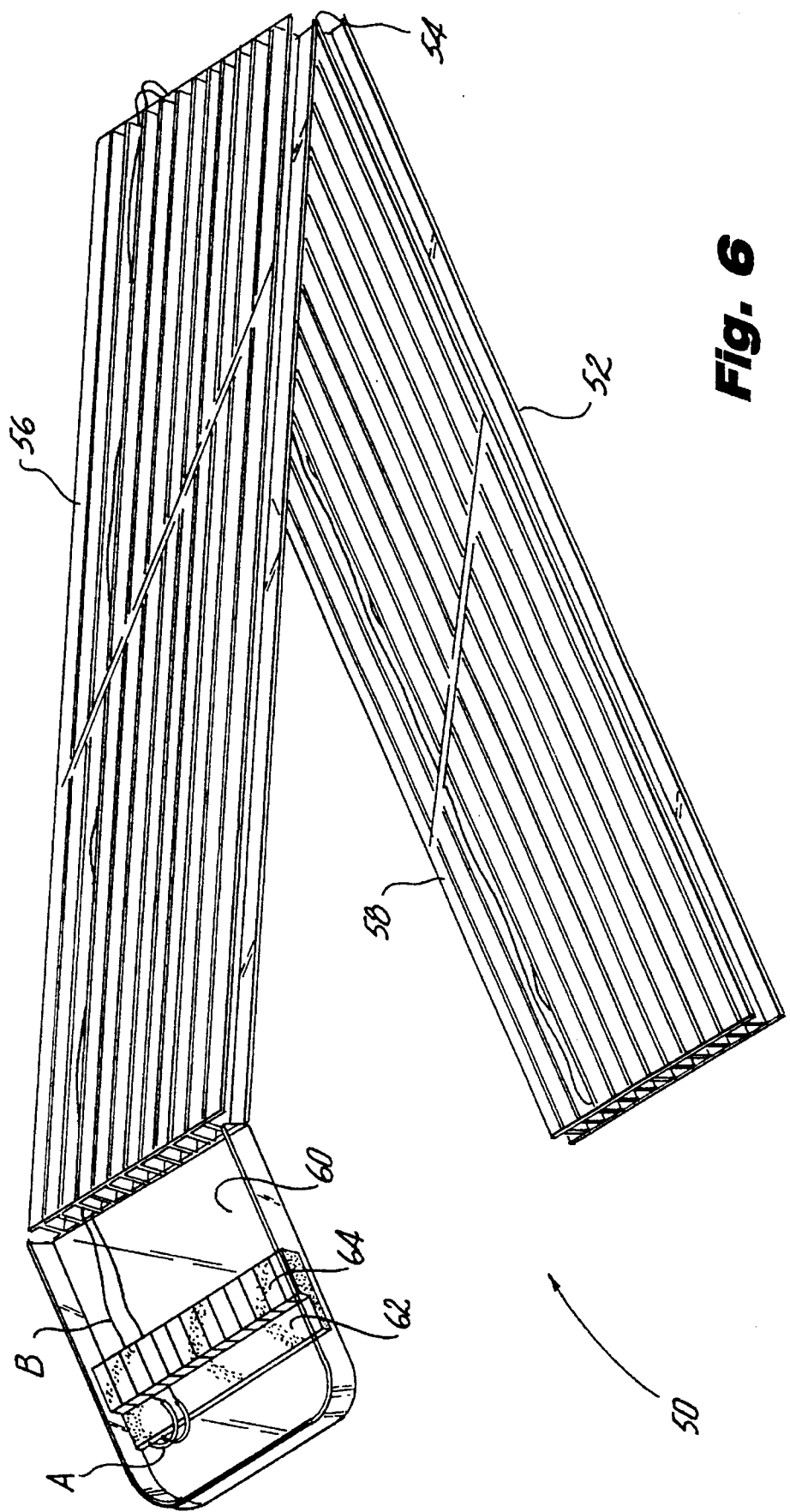

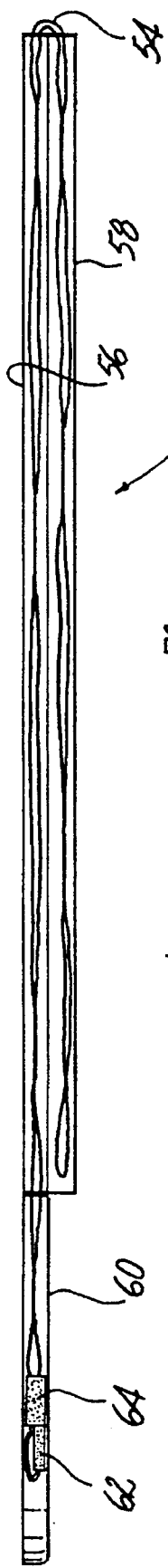
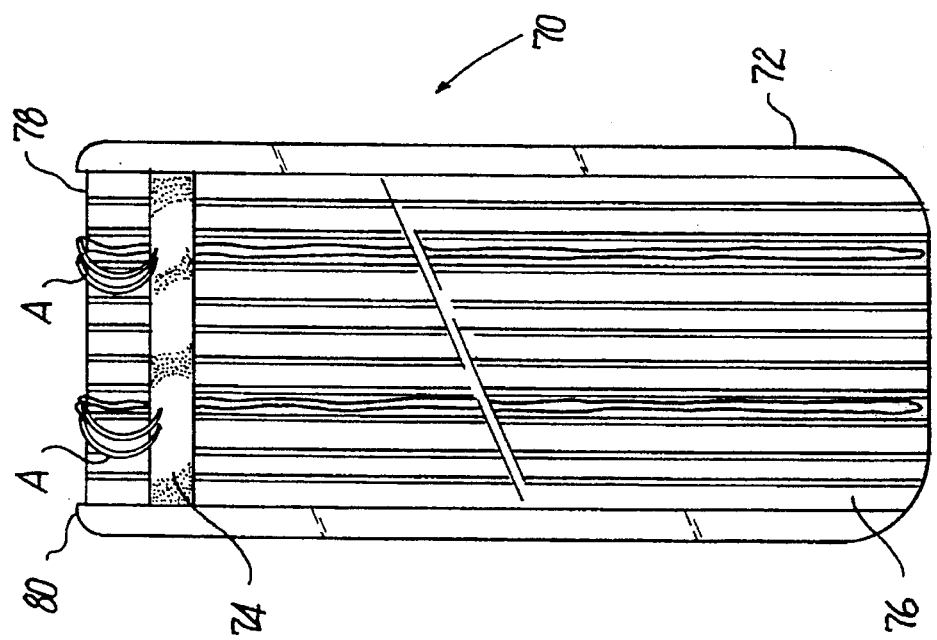
Fig. 7
Fig. 8

SUTURE RETAINER

This is a continuation of application Ser. No. 08/164.522, filed on Dec. 9, 1993 now abandoned.

BACKGROUND OF THE INVENTION

1. Field of the Invention

The present invention is directed to a retainer for storing needled-sutures combinations. More particularly, the present invention relates to a suture retainer defining a plurality of elongated individual suture compartments for storing individual sutures.

2. DESCRIPTION OF THE PRIOR ART

Many types of retainers for sutures and combined surgical needled-suture devices are known in the art. Generally, a retainer should be constructed to adequately secure a needle and suture while providing easy withdrawal during use. It is also preferable to minimize the formation of kinks or bends in the suture during storage.

However, in many of the retainers known heretofore, the sutures are stored in a coiled configuration or a figure eight configuration. Depending on the type of suture material and the duration in which the suture remains in the retainer, the stored suture may assume a set, i.e., the suture may assume the shape in which it is stored. Accordingly, after removal of the suture from the retainer, the suture must be initially straightened in order to perform the desired suturing procedure.

A further objective sought in the design of retainers, particularly retainers intended for storing more than one suture, is to construct the package in a manner such that the delicate sutures are stored and maintained in some form of spaced relation to each other so that access and removal of the suture may be readily available without entanglement of the sutures.

Commonly assigned U.S. Pat. No. 5,123,528 to Brown et al. discloses a package for containing a plurality of combined surgical suture devices in individual storage receptacles. The Brown '528 package includes a backing panel with a molded cover adhesively affixed to the backing panel. The molded cover defines a plurality of elongated blister tracks for accommodating individual flexible sutures. The backing panel includes suture receiving ports and vacuum apertures which communicate with each blister track to facilitate loading and removal of the sutures. Another molded type suture retainer is disclosed in commonly assigned U.S. Pat. No. 5,154,283 to Brown.

Although the retainers described in U.S. Pat. Nos. 5,123, 528 and 5,154,283 have been found to be highly effective for their intended purpose, the present invention is directed to further modifications wherein an elongated suture retainer stores a plurality of sutures with a minimum number of folds or creases in the suture material while maintaining the individuality of each suture with respect to the others.

SUMMARY OF THE INVENTION

Generally stated, the present invention is directed to a suture package for storing a plurality of sutures. The package comprises a molded elongated base member including first and second panel members aligned in general parallel relation and interconnected by a plurality of transverse portions. Adjacent transverse portions define therebetween individual elongated suture compartments for accommodating the sutures.

The elongated compartments are each open at a first end thereof to facilitate insertion and removal of the individual suture portion and may be open at a second end thereof to permit drawing a vacuum on the compartment to facilitate loading with a suture. The suture package may also comprise a retaining panel member which is connected to a transverse edge of the base member.

The retaining panel member includes means for securing needles attached to the individual sutures in generally spaced relation. The preferred needle securing means comprises a foam park affixed to the retaining panel. The foam park is dimensioned, configured and positioned to support at least one needle for each suture whereby the needles are retained by inserting the pointed end of each needle into the foam park.

The retaining panel member may also include means for supporting and retaining the suture end portions extending from each elongated compartment and attached to a respective needle in generally spaced relation. The preferred suture supporting means comprises a foam strip positioned adjacent the needle securing means. The foam strip has a plurality of spaced longitudinal slits with each slit adapted to accommodate and support an individual suture end portion therein.

The suture package may also comprise a cover panel member which is foldably connected along a transverse edge to the retaining panel member. The cover panel member is adapted to fold onto the retaining panel to enclose the needles secured by the needle securing means. Means for retaining the cover panel in the folded condition against the retaining panel is provided. The preferred retaining means comprises at least one tab extending from an upper transverse edge of the cover panel. The tab is dimensioned and positioned to engage an upper transverse edge of the base member when the cover panel is in the folded condition.

In an alternative preferred embodiment, the base member of the package includes first and second base portions foldably connected along a fold line with the first base portion being adapted to fold onto the second base portion. The fold line is disposed approximately at the midline of the base member such that the first and second base portions are substantially equal in length. Such foldable feature of the base member provides a compact package to facilitate storage and handling.

The present invention is also directed to a method for packaging a plurality of individual sutures, comprising the steps of providing a molded base member including a plurality of individual elongated enclosed suture compartments therein with the suture compartments have a first opening at a first end portion thereof for reception of a portion of a suture and a second opening at a second end portion thereof for directing a vacuum therethrough, at least partially inserting an individual suture into a first opening of one of the suture compartments and drawing a vacuum through the corresponding second opening to at least partially assist in drawing at least a substantial portion of the suture into the suture compartment.

BRIEF DESCRIPTION OF THE DRAWINGS

The foregoing features of the present invention will become more readily apparent and may be understood by referring to the following detailed description of illustrative embodiments of the package for surgical sutures and suture-needle assemblies and its novel construction, taken in conjunction with the accompanying drawings, in which:

FIG. 1 is a perspective view of a suture retainer constructed according to the present invention;

FIG. 2 is a partial enlarged plan view of the upper panel of the retainer of FIG. 1 illustrating retention of the needles within the needle park;

FIG. 3 is a partial plan view of the retainer of FIG. 1 illustrating the cover panel in a secured position folded onto the upper panel;

FIG. 4 is a cross-sectional view taken along lines 4—4 of FIG. 1 illustrating the individual suture compartments for storing individual sutures;

FIG. 5 is a perspective view of the retainer of FIG. 1 in a secured position and packaged within an outer pouch;

FIG. 6 is a perspective view of an alternative suture retainer of the present invention including first and second base portions foldably connected along a hinge line;

FIG. 7 is a side elevational view of the retainer of FIG. 6 with the first base portion folded onto the second base portion; and FIG. 8 is a frontal plan view of another alternate embodiment including a needle retaining park affixed to the base member.

DETAILED DESCRIPTION OF THE PREFERRED EMBODIMENTS

Referring initially to FIG. 1, there is illustrated the retainer 10 constructed according to the present invention. Retainer 10 is configured to accommodate a plurality of individual sutures in individual suture compartments defined by the retainer. The retainer is substantially elongated so as to enable the individual sutures to be stored in a single looped configuration thereby reducing the number of bends or kinks formed in the stored suture.

Referring now to FIG. 1, taken in conjunction with the cross-sectional view of FIG. 4, retainer 10 includes molded or extruded plastic base member 12 of generally elongated shape, upper or retaining panel 14 connected along transverse score line 16 to base member 12 and needle cover panel 18 connected along transverse score line 20 to the retaining panel 14. As best illustrated in FIG. 4, base member 12 includes front panel member 22, a rear panel member 24 and a plurality of transverse portions 26 extending between the front and rear panel members 22, 24. Preferably, front and rear panel members 22, 24 and transverse portions 26 are integrally formed and connected by using known molding techniques.

Transverse portions 26 of base member 12 define therebetween adjacent individual suture compartments, identified generally as numeral 28, for storing individual suture portions. In particular, each suture compartment 28 is dimensioned to accommodate an individual flexible suture portion. The suture portion can be disposed therein, with or without being looped, depending on the length of the suture and the length of each compartment 28. Compartments 28 are preferably completely enclosed except for access opening 30 provided at a first end portion of the compartment adjacent upper panel 14 and loading opening 32 disposed at the other end portion of the compartment.

Access opening 30 provides access to compartment 28 to permit the insertion of a portion of the looped suture during loading. Thereafter, a vacuum may be applied to the corresponding appropriate loading opening 32 to assist in drawing the suture into the compartment 28 to complete the loading of the suture into the compartment. Since compartments 28 are preferably completely sealed and enclosed (except for the provision of access and loading openings 30, 32), a vacuum may be applied and maintained within the compartment during the loading procedure. In an alternative method for loading the sutures, sutures may be fed into compartments 28 by hand or with other appropriate suture feeding equipment. In accordance with such method, the sutures may be fed into compartments 28 either via access opening 30 or loading opening 32.

In the preferred embodiment, base member 12 may contain as many as twelve suture compartments 28. The length of base member 12 is approximately seventeen inches. Thus, a suture of at least 34 inches in length may be stored in each compartment 28 in a single looped configuration. With only a single loop in the suture during storage, retainer 10 minimizes undesirable coil set, kinks, etc., which detracts from the utility of the suture for tissue repair.

Referring now to FIGS. 1 and 2, the upper panel 14 of retainer 10 will be discussed in detail. Upper panel 14 is a single panel preferably formed of a resilient plastic material and connected to base member 12 along perforated transverse score line 16. When used to package armed sutures, a needle receiving park 34 is positioned in the general upper portion of retaining panel 14 and is adapted to support a plurality of curved needles A which are connected to sutures B. Needle park 34 is readily pierced by the pointed ends of the needles A to secure the needles within the retainer. Needle park 34 is preferably a strip of foam material which is attached to retaining panel 14 by adhesive means or the like. While pierced foam needle park 34 is preferred, other embodiments of needle parks can be readily adapted to be used with retainer 10.

A suture supporting park 36 is positioned adjacent needle park 34. Suture park 36 is preferably a strip of foam material which includes a plurality of longitudinally oriented slits 38 extending therethrough. Each slit 38 is dimensioned and positioned to accommodate the portion of the respective suture B adjacent attached needle A to secure the suture portion within the suture park. Slits 38 are generally equidistantly spaced from each other to correspondingly position the suture portions of each individual suture B at predetermined intervals. Such particular positioning of slits 38 assists in minimizing the potential for entanglement of the sutures during storage and removal from the retainer. Preferably, two slits 38 are provided for each compartment 28 to retain the two suture end portions extending from each compartment if the suture is looped for storage. The slits 38 for each compartment 28 are generally longitudinally aligned with their respective compartment as shown in FIG. 2.

Referring particularly to FIG. 1, the foam material of needle park 34 is less in dimension (i.e. less thick) than the material of suture park 36 so that the secured needles A may be positioned prostrate against the surface of the needle park 34 in generally parallel relation to retaining panel 14 with the pointed ends of the needles A piercing the upper portions of the park 34. Such secured parallel positioning of needles A enables cover panel 18 to readily fold onto needle retaining panel 14 with minimal obstruction by the secured needles A. Further, the generally flat positioning of secured needles A reduces the overall girth of the secured retainer 10 to facilitate packaging within an outer envelope.

Referring still to FIG. 1, a pair of flaps 40 are connected along opposed sides of upper panel member 14. Flaps 40 are oriented at an angle relative to the plane defined by upper panel 14 and serve to enclose the secured needles A and/or sutures disposed adjacent suture park 36 when cover panel 18 is in the folded condition overlying the upper panel 14 as shown in FIG. 3. A pair of corresponding flaps 42 are also connected along opposed sides of needle cover panel 18. Flaps 42 extend at an angle from cover panel 18 and also serve in enclosing the secured needles A and adjacent suture portions B when needle cover panel 18 is in the folded condition. Flaps 42 of cover panel 18 are dimensioned and oriented to engage the corresponding flaps 40 of retaining panel 14 to assist in retaining the cover panel in the folded secured position. A pair of arcuate locking tabs 44 extend from an upper edge of needle cover panel 18. As best shown in FIG. 3, tabs 44 are dimensioned to be partially received beneath upper panel 22 of base member 12 when cover panel 18 is in the folded position to further assist in retaining the cover panel in this position.

Retainer 10 including base member 12, needle retaining panel 14 and needle cover panel 18 is preferably fabricated from a moldable transparent plastic material such as, for example, polyethylene terephthalate (PETG), Eastman Kodak 6763. Other suitable materials for retainer 10 include polypropylene, polyethylene, polycarbonate, butylate, A.B.S., and styrene. Preferably, base member 12 is formed by extrusion and retaining panel 14 and cover panel 18 are die cut.

Retainer 10 is suitable for storing both absorbable sutures and nonabsorbable sutures, e.g., catgut, silk, nylon, polyester, polypropylene, linen, cotton and absorbable synthetic materials such as polymers and copolymers of glycolic and lactic acids. In the case of nonabsorbable sutures, the sutures and retainer may be enclosed in an outer pouch 46 of the type shown in FIG. 5. Pouch 46 is known as a breather pouch and includes a flat sheet on one side preferably fabricated from TYVEK™ material of DuPont and a plastic laminate sealed to the flat sheet along respective peripheries thereof to form a pocket to accommodate retainer 10. Pouch 46 is suitable for gas sterilization or irradiation sterilization. The upper portion of the laminate terminates in a tab 48 which may be readily grasped by the surgeon to open the outer package. See commonly assigned U.S. Pat. No. 5,220,769 for further disclosure relating to suitable breather pouches.

In the case of absorbable sutures, retainer 10 may be packaged in a foil laminate which would be further packaged within an outer package or breather pouch. An alcohol conditioning fluid may be added to the laminate to preserve the integrity of the suture material if necessary.

FIGS. 6–7 illustrate an alternative embodiment of the present invention. Retainer 50 is substantially similar to the retainer of FIG. 1 and includes an elongated base member 52 having a fold or hinge line 54 disposed at the approximate midline of the base member to define first and second base portions 56, 58. First and second base portions 56, 58 are adapted to fold onto each other to form the compact package illustrated in FIG. 7 so to facilitate storage and handling of the retainer. The length of first and second base portions may range from about 7 inches to 11 inches, with the preferred length of each base portion being about 8 inches. Upper panel 60 having needle park 62 and suture supporting park 64 is substantially similar to upper panel 14 described in connection with FIGS. 1–3.

FIG. 8 illustrates another alternative embodiment of the present invention. Retainer 70 is similar in most respect to the embodiment of FIG. 1 and includes a base member 72 defining a length ranging from about 3 inches to 6 inches, with the preferred length being about 4 inches. A needle park 74, in the form of a foam piece, is adhesively secured to the forward panel member 76 of base member 72. Needle park 74 secures the needles by piercing engagement of the needled ends with the park. An upper portion of base member 72 is removed to form a channel 78 adjacent transverse edge 80 of the base member. Channel 78 accommodates the butt ends of the surgical needles such that the needles may be positioned to overlay the front panel in piercing engagement with needle park 74 while ensuring that the butt ends do not extend beyond the upper transverse edge 80 of the retainer 70. Such positioning of the needles within channel 78 and secured to needle park 74 minimizes the potential for jarring or displacement of the needles from retainer 70 since the needles are retained within the boundaries defined by the retainer.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A suture package comprising on elongated based member including first and second panel members aligned in general parallel relation and interconnected by a plurality of transverse portions, said transverse portions defining therebetween adjacent elongated suture compartments open at a first end thereof to facilitate insertion and removal of a suture portion, a retaining panel member connected to a transverse edge of said base member, a cover panel member foldably connected along a transverse edge to said retaining panel member and adapted to fold onto said retaining panel member, and a pair of opposed flaps disposed along longitudinal sides of said cover panel member.

2. The suture package according to claim 1 wherein said base member is integrally molded of plastic material.

3. The suture package according to claim 1 wherein said elongated compartments are open at a second end thereof to permit drawing a vacuum therein.

4. The suture package according to claim 1 wherein said retaining panel member includes means for securing needles attached to the sutures in generally spaced relation.

5. The suture package according to claim 4 wherein said needle securing means comprises a foam park affixed to said retaining panel.

6. The suture package according to claim 4 wherein said retaining panel member includes means for supporting and retaining the suture end portions extending from said elongated compartments in generally spaced relation.

7. The suture package according to claim 6 wherein said suture supporting means comprises a foam strip positioned adjacent said needle securing means, said foam strip having a plurality of spaced longitudinal slits, each said slit adapted to accommodate and support a suture end portion therein.

8. The suture package according to claim 7 wherein each said elongated compartment is generally longitudinally aligned with two of said slits of said foam strip.

9. The suture package according to claim 1 wherein a pair of opposed flaps are disposed along longitudinal sides of said retaining panel member, said opposed flaps dimensioned and positioned to engage said opposed flaps of said cover panel member to assist in maintaining said cover panel member in a substantially folded closed position.

10. The suture package according to claim 1 wherein each said elongated compartments are dimensioned to accommodate a suture portion in a single looped configuration.

11. The suture package according to claim 10 wherein said base member is approximately seventeen inches in length.

12. The suture package according to claim 1 further comprising needle securing means associated with said base member for securing needles attached to the suture portions.

13. The suture package according to claim 12 wherein said needle securing means comprises a foam park adhered to one of said first and second panel members of said base member.

14. The suture package according to claim 1 wherein said base member includes first and second base portions foldably connected along a fold line, whereby said first base portion is adapted to fold onto said second base portion.

15. The suture package according to claim 14 wherein said fold line is disposed approximately at the midline of said base member such that said first and second base portions are substantially equal in length.

16. The suture package according to claim 1 further comprising means for retaining said cover panel in a folded condition against said retaining panel.

17. The suture package according to claim 16 wherein said retaining means comprises at least one tab extending from an upper transverse edge of said cover panel, said at least one tab dimensioned and positioned to engage an upper edge of said base member when said cover panel is in said folded condition.

18. A suture package and suture comprising, in combination:

a suture package having an elongated base member including first and second panel members aligned in general parallel relation and interconnected by a plurality of transverse portions, the transverse portions defining therebetween adjacent elongated suture compartments open at a first end there of to facilitate insertion and removal of a suture portion, a retaining panel member connected to a transverse edge of said base member, a cover panel member foldably connected along a transverse edge to said retaining panel member and adapted to fold onto said retaining panel member, and a pair of opposed flaps disposed along longitudinal sides of said cover panel member; and at least a portion of at least one suture disposed in any one of the suture compartments.

* * * * *